United States Patent
Nau

[11] Patent Number: 6,057,161
[45] Date of Patent: May 2, 2000

[54] METHOD FOR DETERMINATION OF DRUGS OF ABUSE IN BIOLOGICAL SAMPLES

[75] Inventor: David R. Nau, Manhattan Beach, Calif.

[73] Assignee: Varian, Inc., Palo Alto, Calif.

[21] Appl. No.: 08/958,380

[22] Filed: Oct. 27, 1997

[51] Int. Cl.[7] ................................................. G01N 30/02
[52] U.S. Cl. .......................... 436/96; 436/92; 436/161; 436/178; 436/901
[58] Field of Search ............................. 436/91, 92, 161, 436/178, 901, 96

[56] References Cited

U.S. PATENT DOCUMENTS

| | | |
|---|---|---|
| 3,625,652 | 12/1971 | Fujimoto et al. . |
| 4,145,304 | 3/1979 | Melnick et al. ........................ 252/182 |
| 4,309,286 | 1/1982 | Lenihan et al. . |
| 4,990,458 | 2/1991 | Rosenfeld . |
| 5,062,959 | 11/1991 | Ross et al. ............................... 210/635 |
| 5,104,622 | 4/1992 | Binder . |
| 5,358,641 | 10/1994 | Sanford et al. . |

FOREIGN PATENT DOCUMENTS

| | | |
|---|---|---|
| 249 274 A1 | 9/1997 | Germany . |
| 197 18 652 A1 | 4/1998 | Germany . |
| 60-224698 | 11/1985 | Japan . |
| 9-138226 | 5/1997 | Japan . |

OTHER PUBLICATIONS

Chemical Abstracts (Columbus, Ohio), Abstract No. 86:84312, Wislocki et al., Helath Lab. Sci. (1974), 11(1), 13–19.

Supelco Chromatography Products Catalog (1996), pp. 252–253.

Article by Allen I. Cohen et al., entitled "Determination of Orally Coadministered Nadolol and Its Deuterated Analogue in Human Serum and Urine by Gas Chromatography with Selected–Ion Monitoring Mass Spectrometry", published in *Journal of Pharmaceutical Sciences* in Nov. 1984, vol. 73, No. 11, pp. 1571–1575.

Chen, X.H. et al., "*Isolation of acidic, neutral, and basic drugs from whole blood using a single mixed–mode solid––phase extraction column*," J. Anal. Toxicol. 16: 351–355 (1992).

Goldberger, B.A. et al., "*Confirmatory tests for drugs in the workplace by gas chromatography–mass spectrometry,*" J. Chromatorgr. A 674 (1–2): 78–86 (1994).

Logan, B.K. et al, "*Rapid screening for 100 basic drugs and metabolites in urine using cation exchange solid–phase extraction and high–performance liquid chromatography with diode array detection,*" J. Anal. Toxicol. 14:154–159 (1990).

*Primary Examiner*—Jan Ludlow

[57] ABSTRACT

A high purity styrene-divinyl benzene resin is used for rapid solid phase extraction of drugs of abuse from body fluid samples. Simple extraction procedures are described which provide high recovery and selectivity for a wide variety of drugs. A convenient method of increasing flow rate in such solid phase extractions is also described.

1 Claim, 12 Drawing Sheets

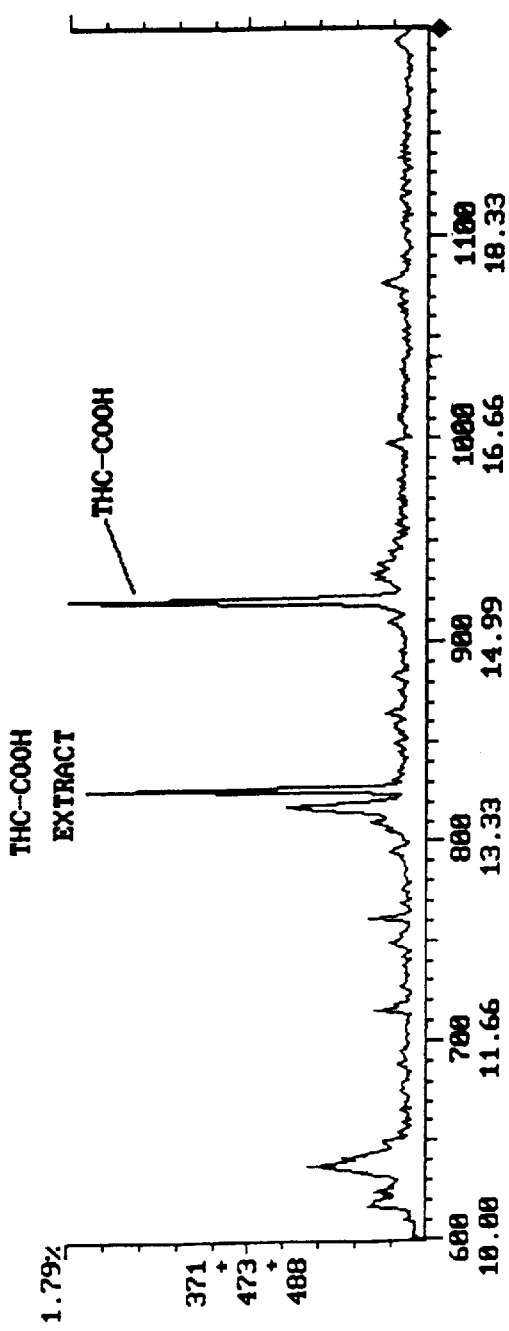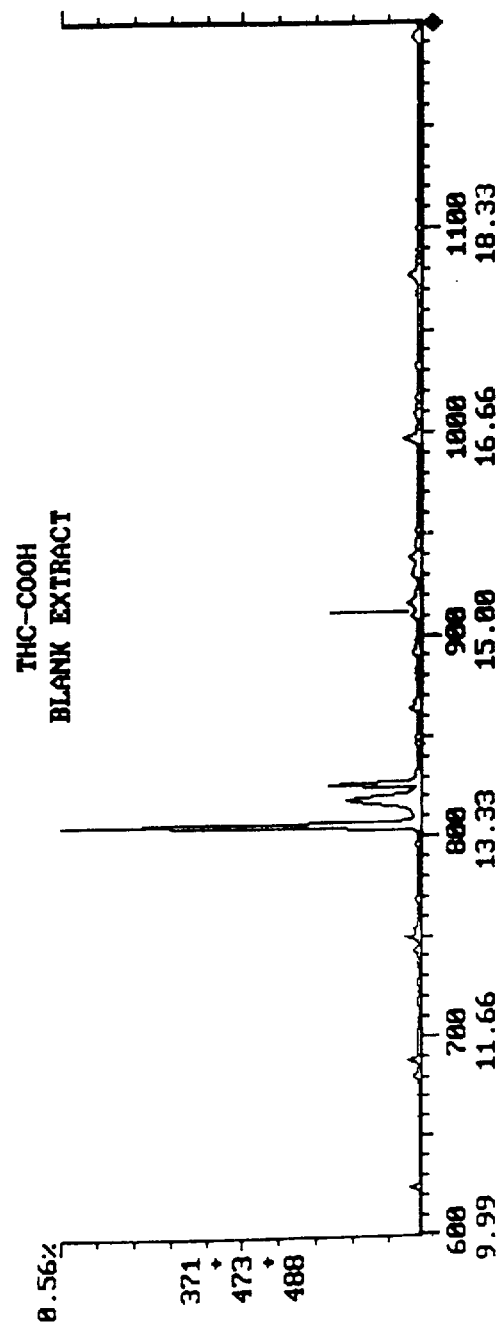

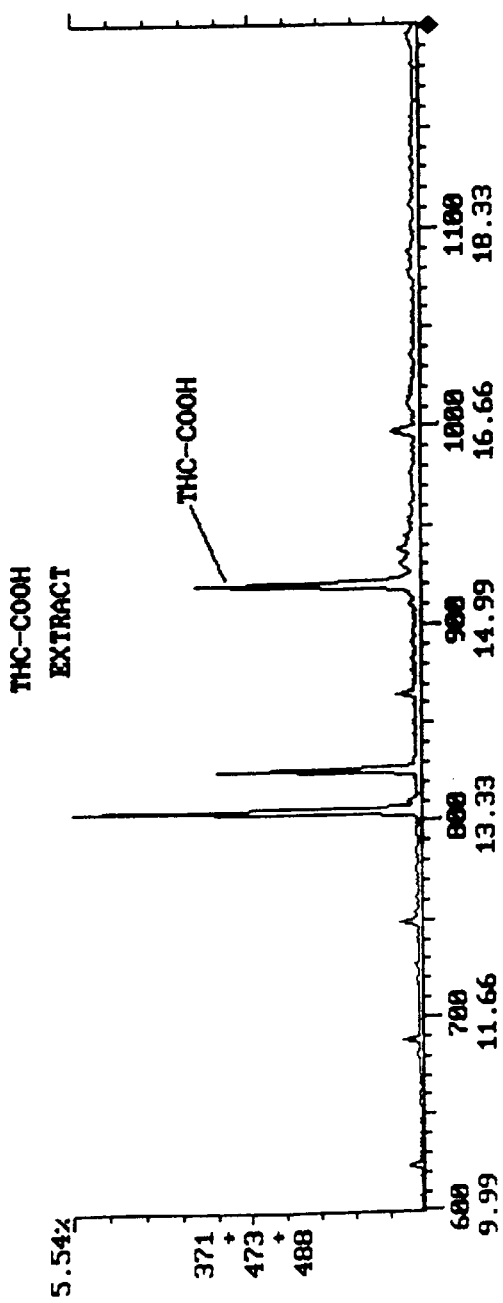
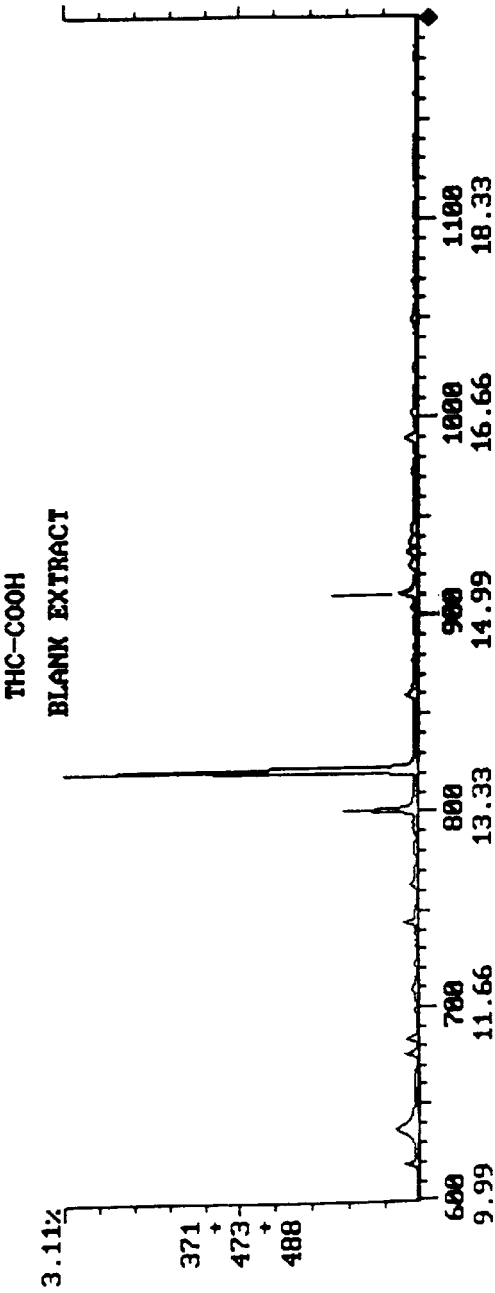

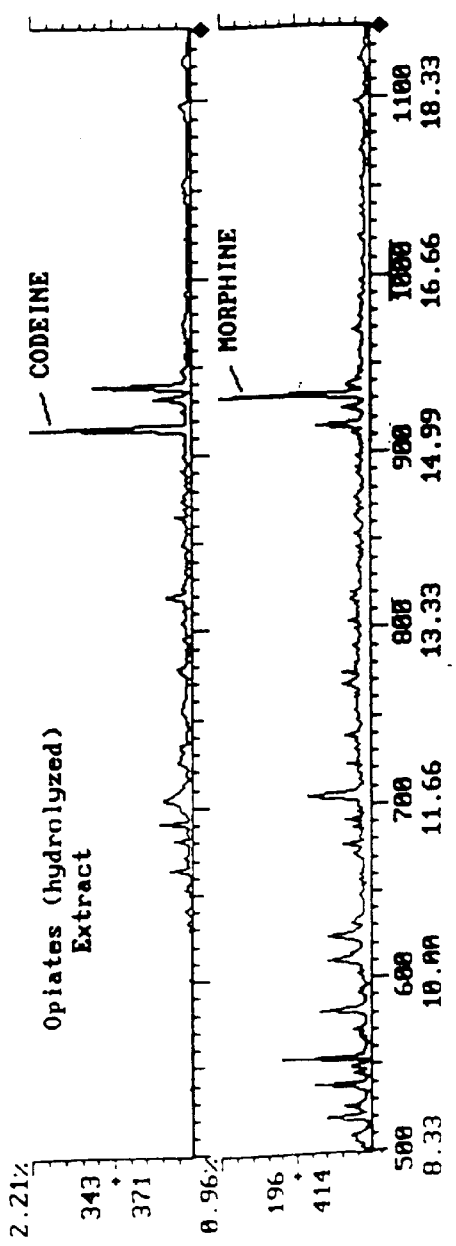
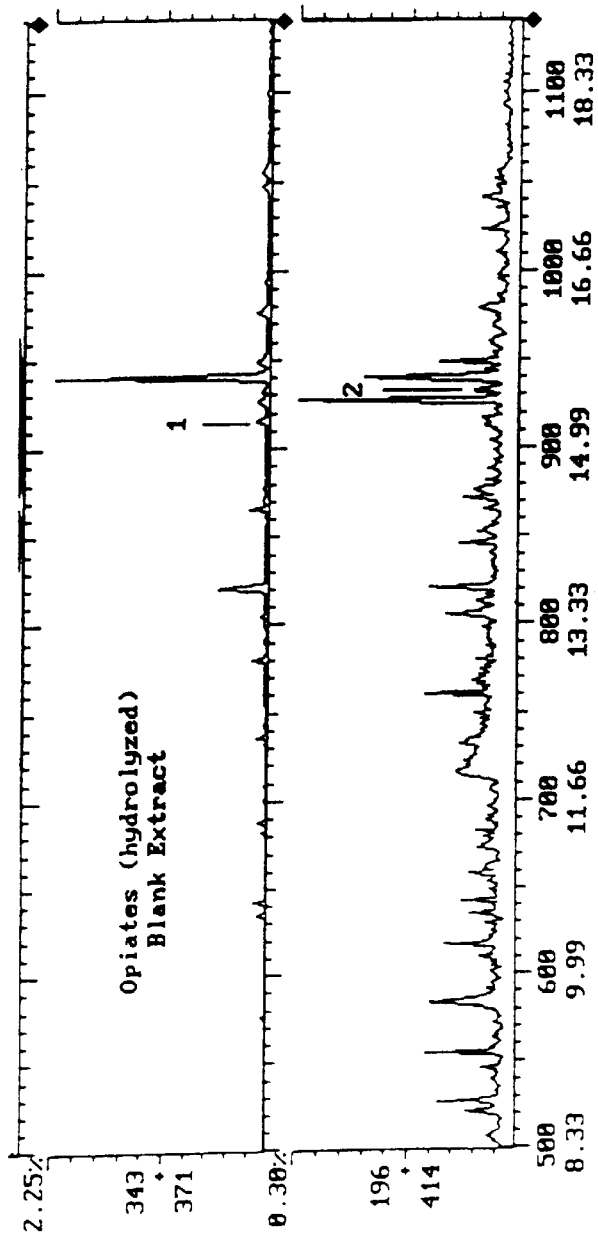
Fig. 4A
Fig. 4B
Fig. 4C
Fig. 4D

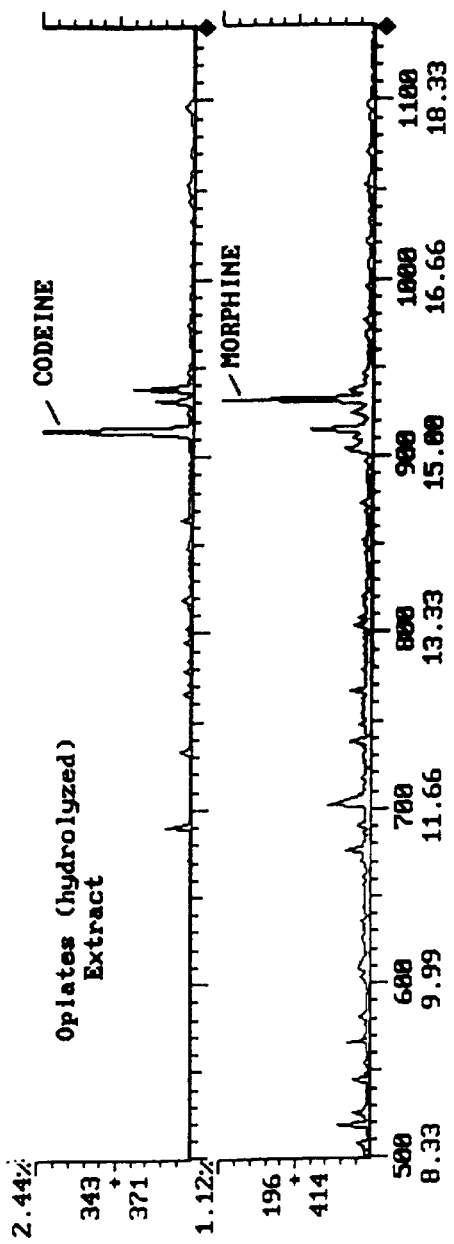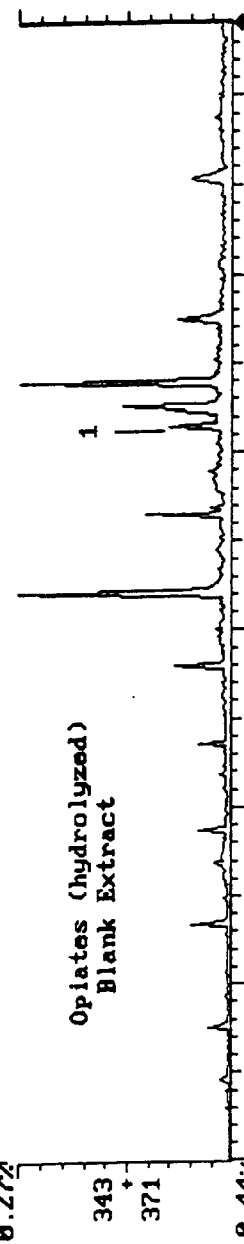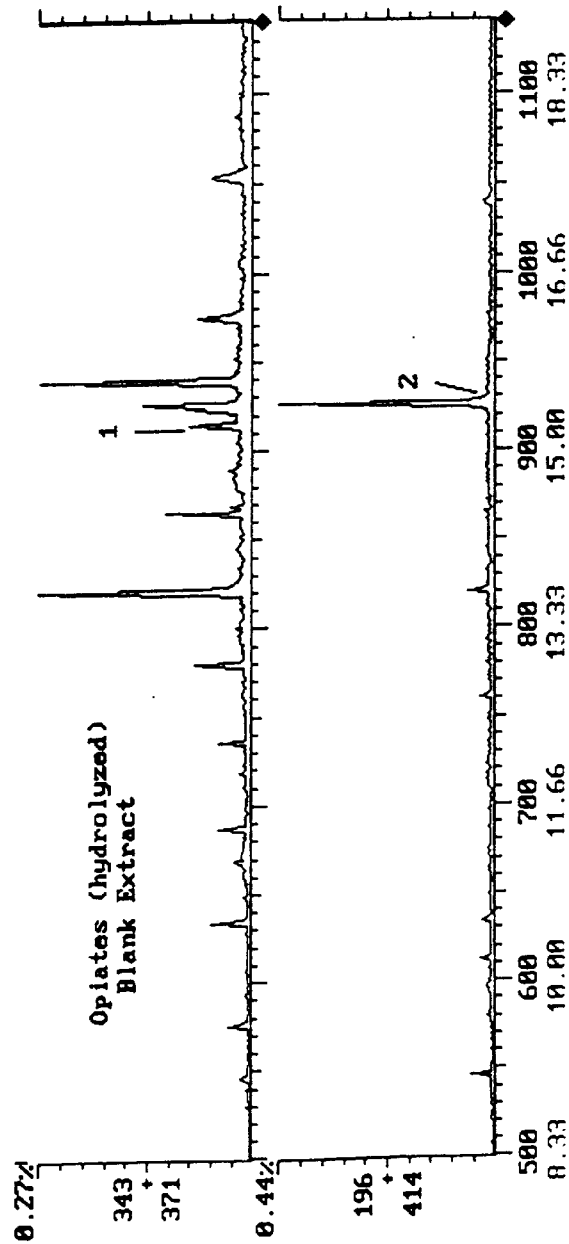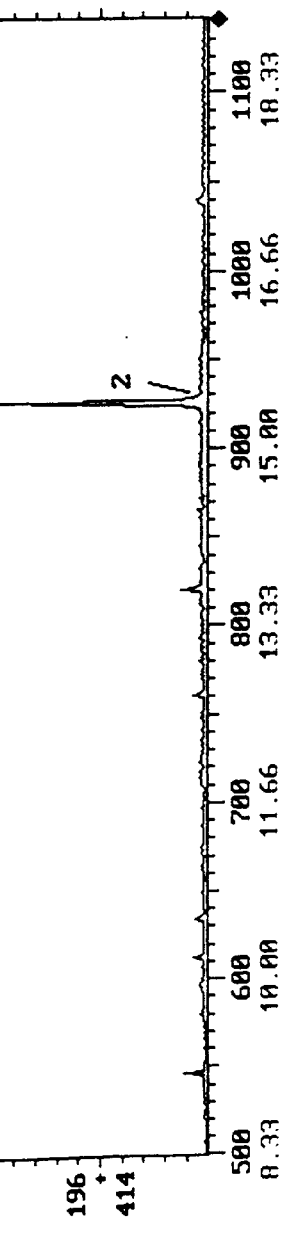

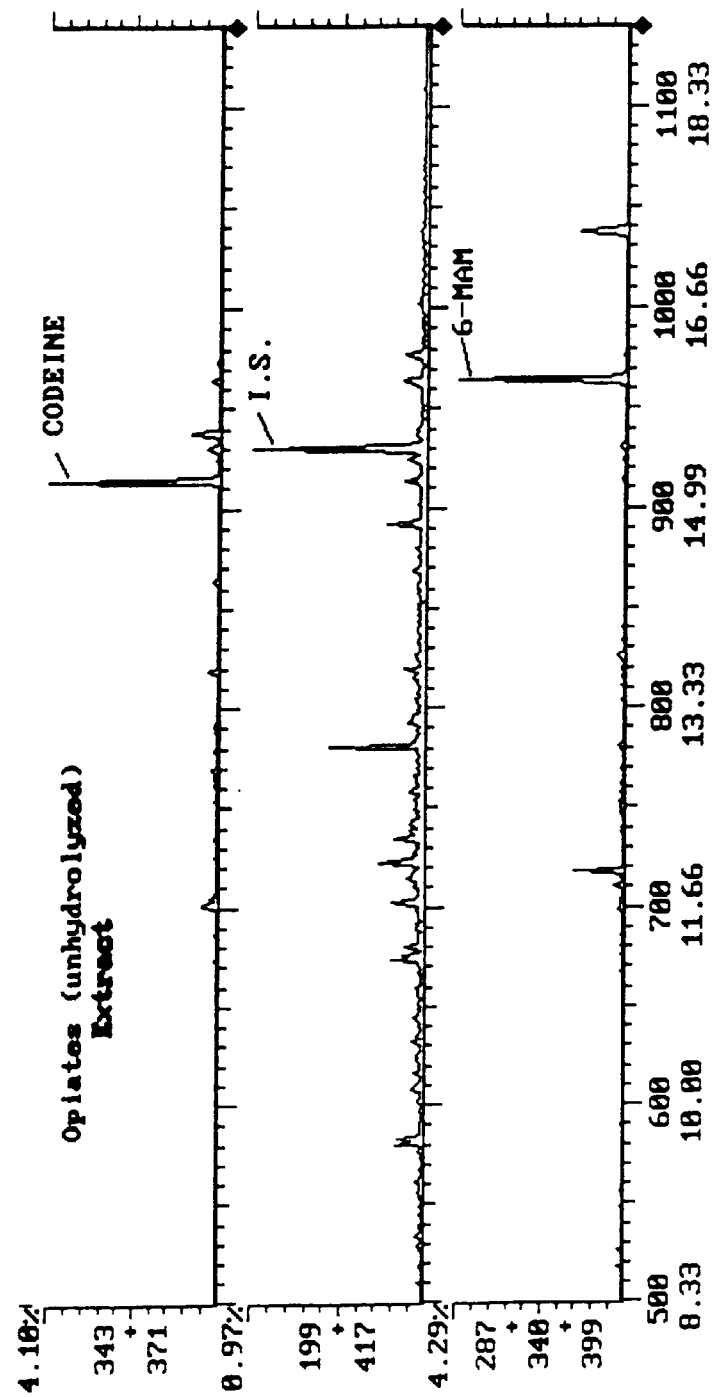

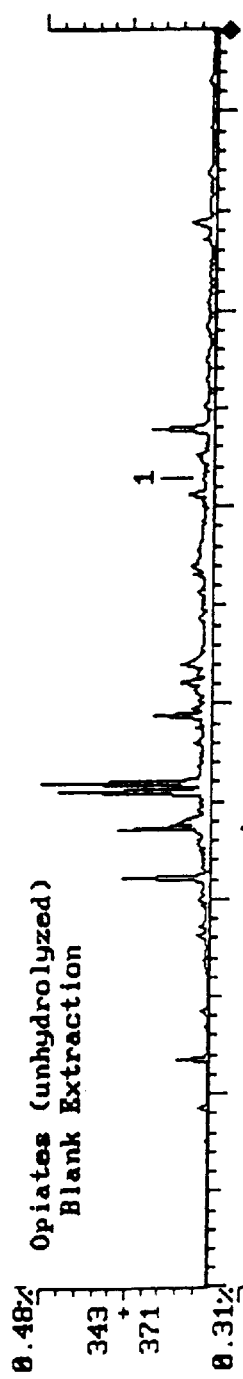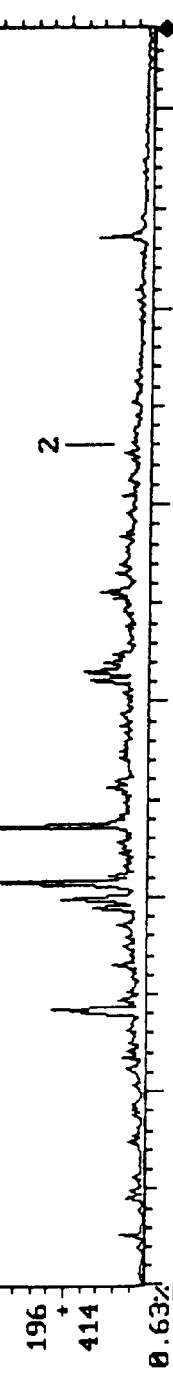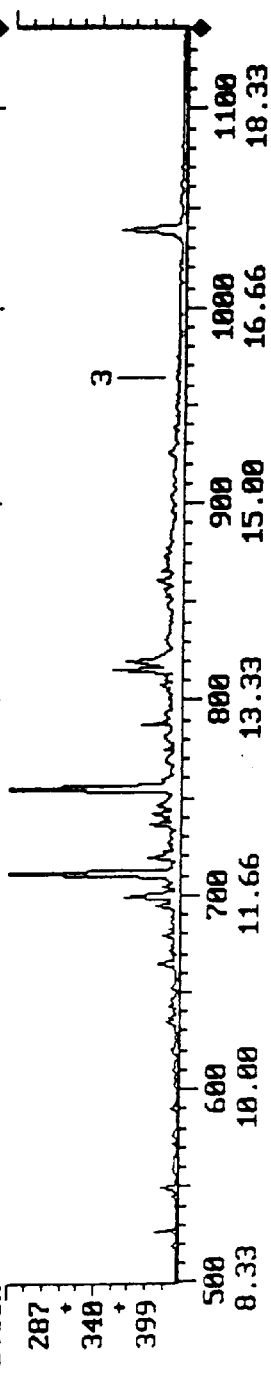

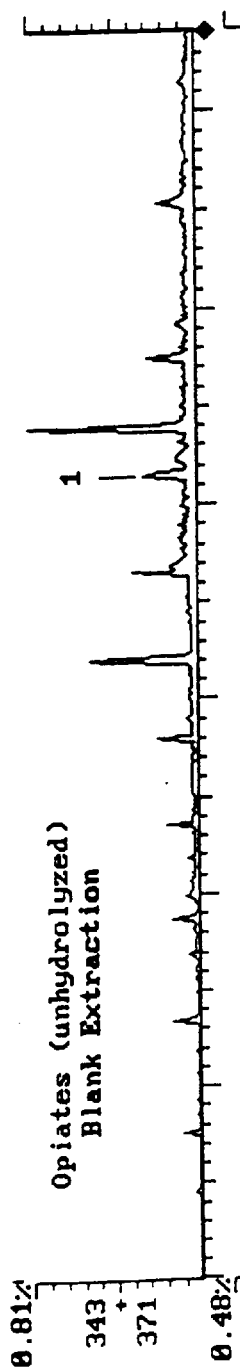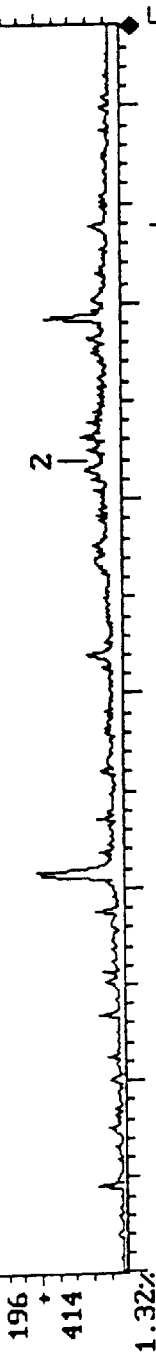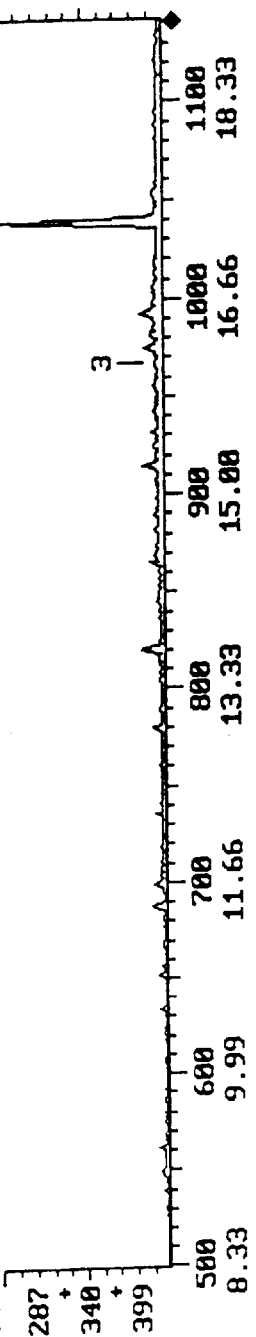
Fig. 9A
Fig. 9B
Fig. 9C

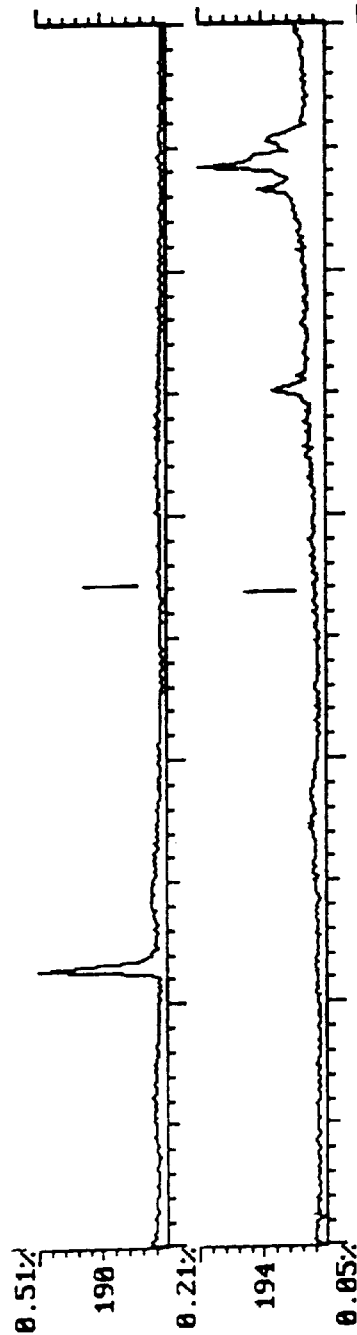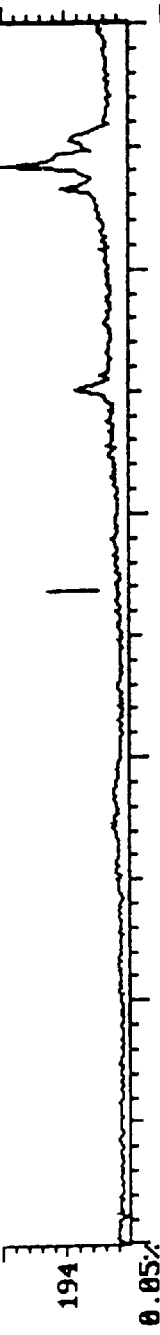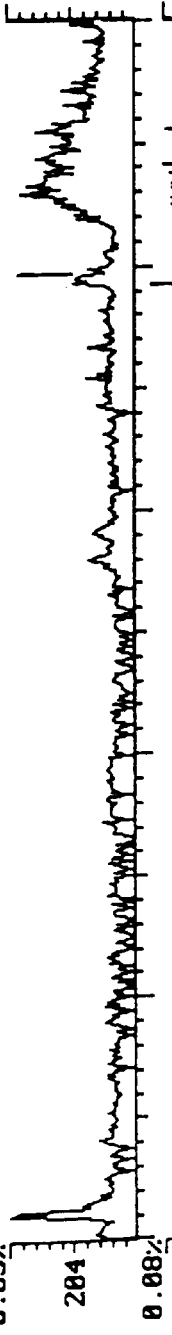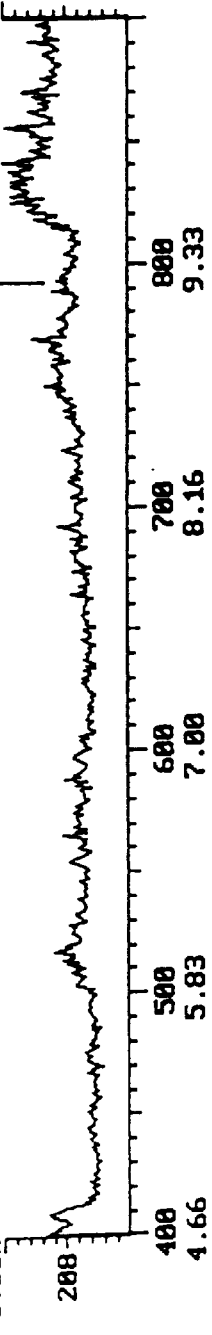

METHOD FOR DETERMINATION OF DRUGS OF ABUSE IN BIOLOGICAL SAMPLES

FIELD OF THE INVENTION

The present invention relates to a method for rapid solid phase extraction of a wide variety of drugs of abuse from body fluid samples. The method provides simple extraction procedures and high recoveries for a variety of drugs using a single adsorbent.

REFERENCES

Chen, X. H. et al., *J. Anal. Toxicol.* 16:351 (1992).
Goldberger, B. A. et al., *J. Chromatogr. A* 674(1–2):73–86 (1994).
Logan, B. K. et al., *J. Anal. Toxicol.* 14:154 (1990).

BACKGROUND OF THE INVENTION

Detection and identification of hazardous or controlled substances in body fluid or tissue samples is an important part of clinical and forensic medicine. The process is often complicated by the large number of endogenous components present in a typical biological sample from which a target substance, or substances, must be isolated. It is desirable for such determinations to be carried out rapidly, with a minimal amount of sample preparation and extraction steps. High sample recovery is needed in detecting trace amounts and for accuracy in quantitation if necessary.

Solid phase extraction (SPE) has largely replaced liquid-liquid extraction methods due to greater convenience and, generally, greater recovery of the substances of interest. Because it is preferable for the same equipment, materials and procedures to be used on the greatest number of different substances to be determined, "mixed mode" extraction media, which include both hydrophobic and polar components, have been introduced. These allow multiple types of interactions with various portions of a drug molecule, i.e. with both hydrocarbon regions and polar or charged sites. In the case of cation- and anion-exchange resins, different resins are used for differently charged analytes.

Typically, however, the use of such mixed-mode supports has required rather complex extraction procedures, using sequences of extraction steps and/or complex solvent mixtures, to selectively bind the compounds of interest, elute contaminants, and then selectively elute the target compounds. Even with the use of such procedures, the recovery of an analyte substance may be low, and interfering endogenous substances may still be co-eluted. Contamination from the support itself can also interfere with the determination.

It is therefore desirable to provide a single support and simple extraction protocols suitable for a wide range of substances to be analyzed, particularly for the detection of drugs of abuse in body fluid samples. Ideally, the extracts are suitable, without further purification, for gas chromatographic (GC), GC-MS (mass spectrometry), or HPLC (high performance liquid chromatography) analysis, thus allowing high turnover with minimal contamination of analytical equipment.

SUMMARY OF THE INVENTION

In one aspect, the invention provides a diagnostic method for determining the presence and/or quantity of a drug of abuse, or a metabolite or derivative thereof, in an aqueous body fluid sample.

According to the method, a body fluid sample, preferably a urine sample, which is suspected of containing an analyte which is a drug of abuse or a metabolite or derivative thereof, is contacted with a substantially underivatized styrene-divinyl benzene resin adsorbent, such that the analyte is adsorbed to the adsorbent. The adsorbent is then washed with a first solvent, or solvent system, which is effective to selectively remove non-analyte components from the adsorbent, while the analyte remains bound to the adsorbent. A second solvent or solvent system, effective to selectively elute the analyte from the adsorbent, is then applied to the adsorbent.

The analyte in the eluate is then detected and/or quantitated. Suitable methods of detecting or quantitating are gas chromatography (GC), GC-mass spectrometry (MS), GC-MS-MS, or HPLC (high performance liquid chromatography). In general, the method produces an eluate which contains about 80% or more, and preferably 90% or more, of the analyte originally present in the sample, and which is suitable, without further purification, for gas chromatographic analysis.

In preferred embodiments of the method, the drug of abuse or metabolite is selected from the group consisting of THC carboxylic acid, heroin, morphine, 6-acetyl morphine, morphine-3-glucuronide, codeine, cocaine, benzoylecgonine, ecgonine methyl ester, amphetamine, methamphetamine, lysergic acid diethylamide (LSD), phencyclidine (PCP), a barbiturate, a benzodiazepine or metabolite thereof, and a tricyclic antidepressant or metabolite thereof. The barbiturate is, for example, butabarbital, pentobarbital, secobarbital, phenobarbital, alphenal, or amobarbital. Benzodiazepines and metabolites for which the method is useful include oxazepam, chlorodiazepoxide, hydroxyalprazolam, and hydroxytriazolam. The tricyclic antidepressant (TCA) may be, for example, doxepin, imipramine, or amitriptyline, and the TCA metabolite may be, for example, nordoxepin, desipramine, or nortriptyline.

The styrene-divinyl benzene adsorbent used for extraction is preferably a high purity resin, such that extraction of about 1.0 g of resin with 10 ml hexane followed by 10 ml methanol yields a residue of less than about 0.2 mg. In preferred methods, less than about 100 mg of resin is used for the extraction of 2 ml of the urine sample.

A preferred solvent combination is that in which the first (wash) solvent is water or 5% aqueous methanol, and the second (elution) solvent is ethyl acetate. Another preferred solvent combination is that in which the first solvent system is a mildly acidic aqueous buffer containing about 10% acetonitrile by volume, and the second solvent system is acetone/chloroform in a ratio of about 1:1 by volume.

When the analyte is THC-COOH, another preferred solvent combination is that in which the first solvent is aqueous acetonitrile, containing about 5% acetonitrile and 1% of a 30% ammonium hydroxide solution, by volume, in water, and the second solvent system is ethyl acetate/isopropyl alcohol in a ratio of about 85:15 by volume.

When the analyte is an opiate or a metabolite or derivative thereof, such as heroin, morphine, 6-acetyl morphine, or codeine, another preferred solvent combination is that in which the first solvent is a mildly acidic aqueous buffer, and the second solvent is methanol containing about 2% of a 30% aqueous ammonium hydroxide solution by volume.

When the analyte is an opiate or a metabolite or derivative thereof, such as heroin, morphine, 6-acetyl morphine, morphine-3-glucuronide, or codeine, and the sample is hydrolyzed before applying it to the adsorbent, another preferred solvent combination is that in which the first solvent is aqueous methanol, containing about 7% methanol by volume in water, and the second solvent system is n-butyl chloride/ethyl acetate in a ratio of about 1:1 by volume, containing about 1% of a 30% ammonium hydroxide solution by volume.

When the analyte is cocaine or benzoylecgonine, another preferred solvent combination is that in which the first solvent is a mildly acidic aqueous buffer, and the second solvent system is acetone/chloroform in a ratio of about 1:1 by volume, or acetonitrile/n-butylchloride in a ratio of about 3:7 by volume.

When the analyte is amphetamine or methamphetamine, another preferred solvent combination is that in which the first solvent is aqueous methanol, containing about 5% methanol by volume in water, and the second solvent is methanol.

When the analyte is a barbiturate, such as butabarbital, pentobarbital, secobarbital, phenobarbital, or amobarbital, another preferred solvent system is that in which the first solvent is a mildly acidic aqueous buffer, and the second solvent system is hexane/ethyl acetate in a ratio of about 3:1 by volume, or acetone/chloroform in a ratio of about 1:1 by volume.

When the analyte is PCP, another preferred solvent combination is that in which the first solvent is a mildly acidic aqueous buffer, and the second solvent system is acetone/chloroform or acetone/methylene chloride, in a ratio of about 1:1 by volume.

When the analyte is a benzodiazepine or metabolite, such as benzodiazepine, oxazepam, chlorodiazepoxide, hydroxyalprazolam, or hydroxytriazolam, another preferred solvent combination is that in which the first solvent is a mildly acidic aqueous buffer, and the second solvent system is acetone/chloroform in a ratio of about 1:1 by volume.

When the analyte is LSD, another preferred solvent combination is that in which the first solvent system is a mildly acidic aqueous buffer containing about 10% acetonitrile by volume, and the second solvent system is acetone/chloroform in a ratio of about 1:1 by volume.

When the analyte is a tricyclic antidepressant or metabolite, such as doxepin, imipramine, amitriptyline, nordoxepin, desipramine, or nortriptyline, another preferred solvent combination is that in which the first solvent is a mildly acidic aqueous buffer or 5% aqueous methanol, and the second solvent system is methylene chloride/isopropyl alcohol in a ratio of about 4:1 by volume or methanol.

In another aspect, the invention provides a method of increasing flow rate of a liquid through a column containing a packed bed of adsorbent, such as in a solid phase extraction, where the column has an outlet tube in communication with the lower surface of the adsorbent bed. In accordance with the method, a tapered tip is provided on the lower end of the outlet tube, thereby facilitating flow through the adsorbent bed and outlet tube via capillary action. In preferred embodiments of the method, the solvent is an aqueous solvent or solution, and the adsorbent is a silica-based adsorbent.

BRIEF DESCRIPTION OF THE DRAWINGS

FIGS. 2A–2B show GC-MS scans of (A) a SDVB extract, prepared in accordance with the invention, of a urine sample with 15 ng/ml added THC-COOH and (B) a similar extract of a blank sample, without added drug;

FIGS. 3A–3B show GC-MS scans of a THC-COOH sample extract and a blank extract, as in FIGS. 2A–2B, prepared on a commercial PMMA (polymethylmethacrylate) extraction column in accordance with the manufacturer's instructions;

FIGS. 4A–4D show (A,C) the codeine ion region and (B,D) the morphine ion region of GC-MS scans of SDVB extracts of (A,B) a hydrolyzed urine sample spiked with each of these drugs at the NIDA detection cutoff level (300 ng/ml) and (C,D) a similar extract of a blank sample, without added drugs;

FIGS. 5A–5D show the corresponding regions of GC-MS scans of PMMA extracts, prepared in accordance with the manufacturer's instructions, of (A,B) a hydrolyzed codeine/morphine sample and (C,D) a blank extract, as in FIGS. 4A–4D;

FIGS. 6A–6C show the codeine, internal standard, and morphine ion regions, respectively, of a GC-MS scan of an SDVB extract of an unhydrolyzed urine sample spiked with each of these drugs at the NIDA detection cutoff level (300 ng/ml);

FIGS. 7A–7C show the corresponding regions of a GC-MS scan of an SDVB extract of a blank unhydrolyzed urine sample, without added drugs;

FIGS. 9A–9C show the corresponding regions of a GC-MS scan of a PMMA extract, prepared in accordance with the manufacturer's instructions, of a blank unhydrolyzed urine sample, without added drugs;

FIGS. 11A–11D show the corresponding regions of a GC-MS scan of an SDVB extract of a blank urine sample, without added drugs.

DETAILED DESCRIPTION OF THE INVENTION

I. Definitions

Figure 1:
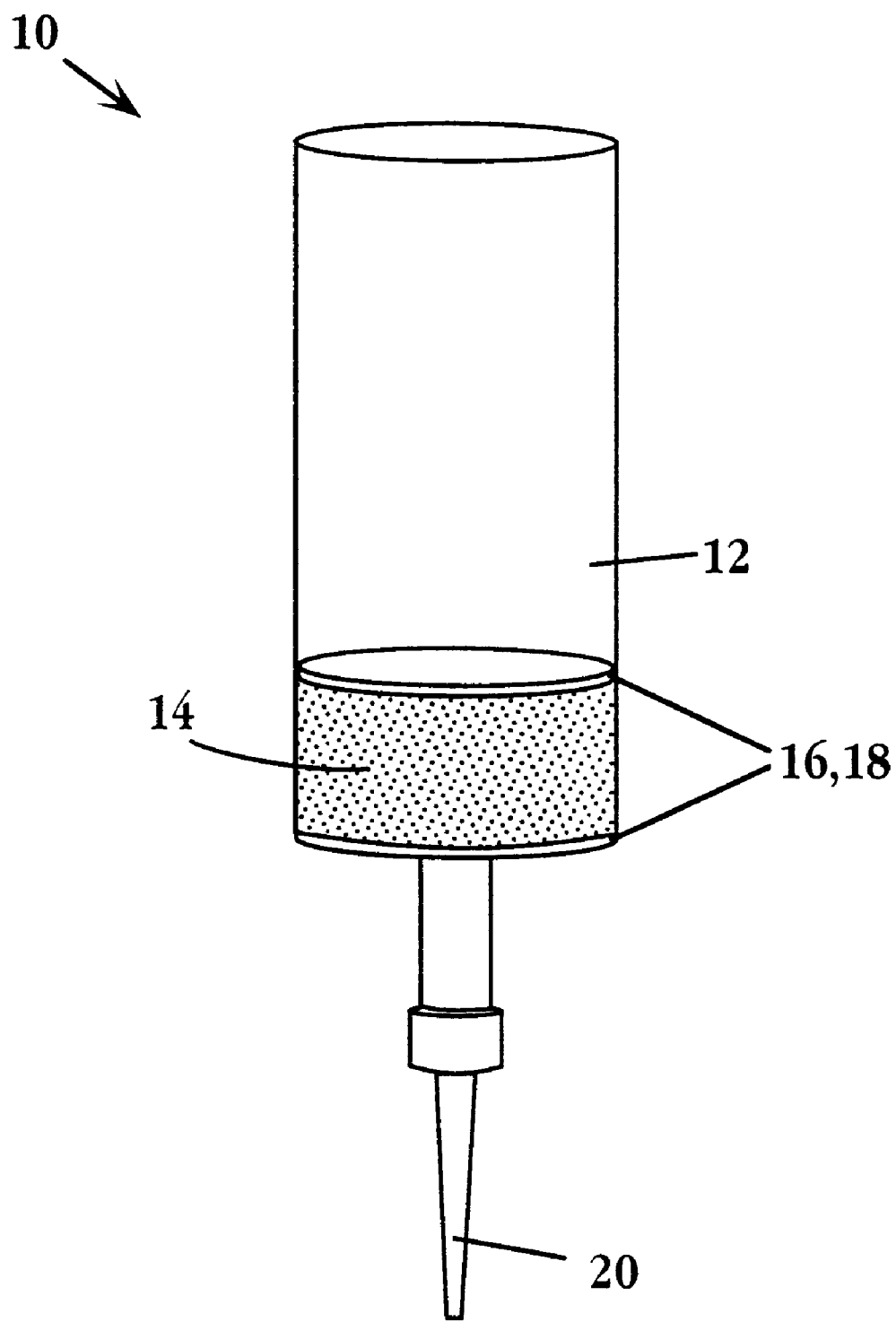
FIG. 1 shows a preferred configuration of an extraction column used to carry out the extraction methods of the invention.

The terms below have the following meanings unless indicated otherwise.

"Drugs of abuse" include illicit drugs, as well as prescription drugs that are subject to abuse or addiction, such as stimulants, tranquilizers, and antidepressants. Examples are THC (tetrahydrocannabinol), heroin, morphine, codeine, cocaine, amphetamine, methamphetamine, LSD (lysergic acid diethylamide), PCP (phencyclidine), barbiturates, such as butabarbital, pentobarbital, secobarbital, phenobarbital, alphenal, and amobarbital, benzodiazepines, such as oxazepam and chlorodiazepoxide, and tricyclic antidepressants, such as doxepin, imipramine, and amitriptyline. The method also applies to common metabolites and derivatives of these substances, as described in Section III below.

As used herein, a "solvent system" may refer to a single solvent or to a mixture of solvents.

"Gas chromatographic (or GC) analysis" includes GC and GC-based methods such as GC-MS, GC-MS-MS, GC-FID, etc.

II. Solid Phase Extraction Support

A. Adsorbent

In accordance with the invention, the body fluid sample suspected of containing a drug of abuse, or metabolite thereof, is contacted with an adsorbent surface of a substantially underivatized styrene-divinyl benzene (SDVB) resin, also referred to as crosslinked polystyrene. By "substantially underivatized" is meant that fewer than about 2% of the styrene moieties of the polymer are substituted with groups other than the DVB crosslinking group. Preferably, the resin is 100% underivatized. Suitable SDVB resins are commercially available from sources such as Mitsubishi Chemicals, Rohm and Haas, The Purolite Company, and Polymer Laboratories, Inc.

Resins having various particle sizes and porosities are available. For the present application, particles ranging in size from 5 $\mu$m to 1000 $\mu$m may be used; however, sizes greater than 50 $\mu$m are preferred, to reduce the problem of "fines" penetrating frits or filters, and to give acceptable flow rates. Sizes of 100–200 $\mu$m are particularly preferred. Particles having pore sizes of greater than 20Å and up to 10,000Å may be used; pore sizes of 100–500Å are preferred.

For optimum results, the resin is cleaned prior to use to give a high purity adsorbent. In a representative cleaning procedure, the resin is soaked overnight in toluene, filtered, soaked overnight a second time in toluene, filtered, soaked overnight in acetone, filtered, and oven dried. In an alternate procedure, the resin is soaked overnight in 7:3 n-butyl chloride/acetonitrile and then washed at least two times with isopropyl alcohol. After such cleaning, extraction of a 1 g sample of the adsorbent with 10 ml methanol followed by 10 ml hexane, or with 1:1 n-butyl chloride/acetonitrile (20 ml solvent per gram of resin), followed by evaporation of the solvent, typically produces a residue of 0.5 mg or less, and preferably 0.2 mg or less. Additionally, extraction of a 1 g sample with $CH_2Cl_2$ preferably produces less than 1 $\mu$g of any given component as measured by GC-FID (flame ionization detection) analysis.

The use of this high-purity resin minimizes contamination from the resin during a sample determination. Such contamination could otherwise interfere in determining the amount of analyte extracted from a sample, or in identifying an analyte, if, for example, a contaminant had a similar GC retention time and/or ion molecular weight to that of an analyte. With respect to the drug determination methods described herein, GC-MS analysis of resin extracted as described above showed no significant interference with key ions for the analyte substances.

Previously reported extraction methods using polystyrene adsorbents have routinely added a purification step, e.g. preparative thin-layer chromatography of the eluate, before GC analysis is performed. Because of the minimal contamination from the adsorbent and the high selectivity of the solvent systems used in the present methods, the eluates produced may be used directly for GC-based analysis, after any desired derivatization of the analytes.

B. Column Configuration

Although different types of column materials and configurations may be employed, a conventional, short-path chromatography column, as illustrated at 10 in FIG. 1, is inexpensive and suitable for easy packing and elution. The column 12 may be conveniently derived from a syringe barrel. The adsorbent 14 is preferably sandwiched between two porous frits, as shown at 16 and 18. The column and frits are preferably constructed of a sturdy, non-swelling plastic such as polyethylene, polypropylene, or Teflon®. Glass columns and Teflon® frits may also be used, particularly for applications requiring high purity. In addition to being non-swellable in the solvents used for extraction, the column and frit components are preferably manufactured and cleaned, as necessary, such that they contain a minimum amount of leachable materials.

Because the extraction method employs gravity flow of solvents, no pressure-applying means are required. However, it is desirable to provide a means of applying vacuum to the column outlet, or positive pressure to the column inlet, for drying the sorbent bed, or to enhance flow rate and sample throughput.

For determination of drugs of abuse in a body fluid sample, such as a urine sample, a column having a capacity of 3 ml, approximately 1 cm in internal diameter, is typically used for a 2 ml fluid sample. The amount of adsorbent is preferably 50 to 200 mg resin per 2 ml sample, and more preferably less than 100 mg. This amount is found to give high solute recovery without unacceptable reductions in flow rate. Flow rate may be increased, if desired, by increasing the diameter of the column. Too large a diameter, however, will result in a very low bed height, making it difficult to produce a uniform and consistent packing.

A useful column modification for increasing flow rate, particularly for columns employing a small particle size absorbent or finer frits, is illustrated in FIG. 1. A tapered tip 20, such as a pipette tip, is added to the bottom of the outlet tube, as shown, and facilitates flow via capillary action. For example, flow times were measured for flow of an aqueous sample (2 ml urine+1.5 ml buffer) through 3 cc capacity columns containing, respectively, 75 mg of a silica based adsorbent (Bond Elut Certify® HF, from Varian Sample Preparation Products, Harbor City, Calif.) and 50 mg of a styrene-divinylbenzene adsorbent as described herein. The adsorbent in each case had a particle size of about 150$\mu$ and was contained by a 20$\mu$ frit. In this experiment, the pipette tips used were about 4.5 cm in length, having an upper i.d. of about 0.4 cm, an i.d. at the lower outlet of about 0.1 cm, and an internal volume of about 200 $\mu$l. Flow times are shown in Table I.

As the data shows, modification of the column as described above significantly improved flow time for the aqueous sample, particularly for the silica-based adsorbent. Since flow of the aqueous sample through the hydrophobic SDVB is already fairly rapid, the column modification had less of an impact in this case.

TABLE I

| Column Modified | Flow Times, min. | |
|---|---|---|
| | 75 mg silica | 50 mg SDVB |
| No | 15.3 | 5.0 |
| Yes | 3.3 | 3.7 |

III. Sample Preparation

As is routine in analysis of body fluid samples, the sample generally undergoes a pretreatment to remove possibly interfering components, such as proteins or particulates, to adjust the pH or ionic strength of the sample for optimum extraction, or simply to dilute the sample. In analysis of opiates, the sample is often hydrolyzed, e.g. by treatment with aqueous acid.

Such pretreatment methods are well known in the art (see e.g. Goldberger, Chen, Logan). Blood product samples and urine are typically diluted with a buffer solution. For blood samples, sonication may be used to fragment cells. Proteins may be precipitated by addition of, for example, organic solvents, perchloric or trichloroacetic acid, or metal ions; however, such precipitation may cause loss of analyte via coprecipitation.

IV. Analytes

The preferred analytes for the present method are compounds referred to as drugs of abuse. These include the so-called "street drugs", or illicit drugs, as well as sedatives, antidepressants, etc., which are available by prescription but subject to abuse or addiction. Specific classes of drugs which can be analyzed according to the present method include the following:

1. THC (tetrahydrocannabinol)
   THC carboxylic acid*
2. Cocaine
   Benzoylecgonine*
3. Amphetamine
   Methamphetamine
4. Barbiturates, which include:
   Butabarbital
   Pentobarbital
   Secobarbital
   Phenobarbital
   Amobarbital
   Alphenal
5. PCP (phencyclidine)
6. Opiates, which include:
   Codeine
   Heroin
   Morphine
   MAM (6-acetylmorphine)*
   Morphine-3-glucoronide*
7. Benzodiazepines, which include:
   Oxazepam
   Chlorodiazepoxide
   Hydroxyalprazolam*
   Hydroxytriazolam*
8. LSD (lysergic acid diethylamide)
9. Tricyclic antidepressants (TCA's), which include:
   Nordoxepin*
   Doxepin
   Desipramine*
   Nortriptyline*
   Imipramine
   Amitriptyline

* metabolite

Also included, as indicated, are various metabolites or derivatives of the native drugs, which are often the primary substances detected, due to rapid metabolism of a drug in the body. For example, THC (11-nor-Δ-9-tetrahydrocannabinol), the major psychoactive component in marijuana, is rapidly accumulated in body tissues, due to its lipophilic nature, and is difficult to detect in blood or urine. However, its major metabolite, THC-carboxylic acid, is excreted in the urine as a glucuronic acid conjugate at detectable levels.

Cocaine is rapidly metabolized in the body to benzoylecgonine, ecgonine methyl ester, and other minor metabolites. Benzoylecgonine can be detected in the urine for a longer period of time than ecgonine methyl ester, and thus its detection is the primary means of screening for cocaine use.

The most common opiates are morphine, heroin, and codeine. Morphine is also the major metabolite of codeine. A major metabolite of heroin, 6-acetylmorphine, also termed monoacetylmorphine, MAM or 6-MAM, is formed by deacetylation of heroin (3,6-diacetyl morphine), which occurs rapidly after intake. MAM is further metabolized to morphine and morphine-3-glucoronide. All three of these products, as well as traces of native heroin, can be found in the urine up to 40 hours after administration of heroin.

V. Extraction Methods

A. Procedures

In accordance with the method, a body fluid sample suspected of containing a drug of abuse or metabolite, particularly one of the above listed analytes, is pretreated as necessary and applied to a column of high purity, substantially underivatized SDVB resin. Upon contact with the resin, analyte components, and typically other components of the sample, adsorb to the resin. The resin is then washed with a solvent or solvent system which is effective to selectively remove some or all non-analyte components, while the analyte remains bound to the resin.

After washing, a second solvent is applied which is effective to selectively elute the analyte compound(s) from the column. Preferably, only these compounds are eluted, but, in general, solvents are selected such that no compound which would interfere with the subsequent determination of the analyte is eluted to any significant extent.

The operations of washing of the column, applying the sample, and eluting the sample are preferably done under gravity-flow conditions. Vacuum is frequently used for drying the column between these operations, and a light vacuum may be used to draw solutions through the column. However, application of high vacuum is not required.

Examples 1–10 below describe methods and preferred solvent systems for detecting common drugs of abuse, or their metabolites, in the urine. The procedures described require only one wash step and one elution step, in contrast to many procedures currently used in the field, e.g. on mixed-mode columns, where several such steps may be required.

In many of these methods, a wash with a mildly acidic aqueous buffer is used. The pH of the buffer is preferably in the range of about 4.5 to about 6.5; a representative pH of 6.0 is used in the examples. Preferred proportions of solvent mixtures are given in the examples; however, slight variations from these proportions can generally be made without significantly affecting recovery or selectivity. In addition, decreasing the volume of the sample dilution buffer, the column conditioning solvent, the wash solvent, or the elution solvent did not have a major effect, in most cases, on the recovery or purity of the final products.

B. Analyte Recoveries

According to a further advantage of the method, high recoveries are achieved. Recoveries of analytes obtained using the methods described in the Examples are given in Table II. As shown in the table, 80% or greater, and in many cases, 90% or greater of the analyte present in the body fluid sample is typically recovered in the eluate.

In some cases, recoveries somewhat greater than 100% are seen. This is generally due to the presence of trace contaminants, and/or to minor errors in quantitation based on the internal standard.

Although large numbers of solvent systems were tested, those described in the Examples were found to give the best combination of recovery, as shown in Table I, and selectivity, as shown in the GC-MS and HPLC scans discussed below, for selected groups of analytes. Certain solvent systems, such as those described in Examples 8 and 10, gave good results for a wide variety of analytes.

TABLE II

| Analyte | Example No.; Percent Recovery | | | | | | |
|---|---|---|---|---|---|---|---|
|  | <u>1</u> | <u>10</u> |  |  |  |  |  |
| A. THC—COOH | 95 | 100 |  |  |  |  |  |
|  | <u>2A</u> | <u>2B</u> | <u>10</u> |  |  |  |  |
| B. Cocaine | 100 | 100 | 81 |  |  |  |  |
| Benzoylecgonine | 100 | 99 | 74 |  |  |  |  |
|  | <u>3</u> | <u>10</u> |  |  |  |  |  |
| C. Amphetamine | 92 | 85 |  |  |  |  |  |
| Methamphetamine | 96 | 100 |  |  |  |  |  |
|  | <u>4A</u> | <u>4B</u> | <u>10</u> |  |  |  |  |
| D. Butabarbital | 91 | 100 | 90 |  |  |  |  |
| Pentobarbital | 93 | 87 | 73 |  |  |  |  |
| Secobarbital | 83 | 100 | 92 |  |  |  |  |
| Phenobarbital | 91 | nd | nd |  |  |  |  |
| Amobarbital | nd* | 93 | 90 |  |  |  |  |
| Alphenal | 105 | nd | nd |  |  |  |  |
|  | <u>5A</u> | <u>5B</u> | <u>10</u> |  |  |  |  |
| E. PCP | 100 | 100 | 100 |  |  |  |  |
|  | <u>6A</u> | <u>6B</u> | <u>6C</u> | <u>6D</u> | <u>6E</u> | <u>6F</u> | <u>10</u> |
| F. Codeine | 85 | 98 | 95 | 77 | 82 | 92 | 85 |
| Morphine | 84 | 103 | 57 | 83 | 82 | 73 | 80 |
| MAM | 75 | 92 | 71 | 63 | nd | nd | 83 |
|  | <u>7</u> | <u>10</u> |  |  |  |  |  |
| G. Oxazepam | 41 | 85 |  |  |  |  |  |
| Chlorodiazepoxide | 100 | 100 |  |  |  |  |  |
| Hydroxyalprazolam | 100 | 100 |  |  |  |  |  |
| Hydroxytriazolam | 100 | 100 |  |  |  |  |  |
|  | <u>8</u> | <u>10</u> |  |  |  |  |  |
| H. LSD | 90 | 100 |  |  |  |  |  |
|  | <u>9A</u> | <u>9B</u> | <u>9C</u> | <u>9D</u> |  |  |  |
| J. Nordoxepin | 93 | 84 | 91 | 80 |  |  |  |
| Doxepin | 94 | 85 | 80 | 69 |  |  |  |
| Desipramine | 98 | 104 | 105 | 85 |  |  |  |
| Nortriptyline | 89 | 87 | 93 | 86 |  |  |  |
| Imipramine | 95 | 84 | 82 | 72 |  |  |  |
| Amitriptyline | 100 | 92 | 95 | 77 |  |  |  |

*nd = not determined

In contrast to these results, a widely used commercial extraction system, which employs a poly(methyl methacrylate) (PMMA)-based adsorbent, gave the following recoveries, using extraction protocols supplied by the manufacturer (Biochemical Diagnostics, Inc., Edgewood, N.Y.). Both original (dated 1995) and revised (dated 1997) extraction protocols were tested.

|  | Original | Revised |
|---|---|---|
| THC—COOH | 50% | 60% |
| Cocaine | 87% | 10% |
| Benzoylecgonine | 14% | 90% |
| Codeine | 100% | 66% |
| Morphine | 26% | 44% |
| 6-MAM | 111% | 39% |

As can be seen, neither protocol produced high recovery for THC-COOH or morphine, and the recovery of 6-MAM was low for one protocol, while the other showed evidence of probable contamination.

C. Detection Limits

Table III gives approximate minimum detection limits, using methods described in the Examples noted, for the classes of drugs shown in Table II. Where multiple drugs are listed, the detection limit shown is for the drug with the highest level of contamination. All limits are at or below the NIDA (National Institute on Drug Abuse) cut off level (if any) for the drug class.

TABLE III

| Drug Name | ng/ml urine (Example No.) | NIDA cutoff level, ng/ml |
|---|---|---|
| THC—COOH | 8 (1) | 15 |
| cocaine |  |  |
| benzoylecgonine | 96 (2A–B) | 150 |
| oxazepam |  |  |
| chlorodiazeoxide | 12 (7) |  |
| 7-aminoclonazepam | 15 (10) |  |
| hydroxytrazolam |  |  |
| codeine |  |  |
| morphine | 100 (6E) | 300 |
| 6-monoacetylmorphine | 16 (10) |  |
| amphetamine |  |  |
| methamphetamine | 75 (3) | 300 |
|  | 5 (10) |  |
| nordoxepin |  |  |
| doxepin | 50 (9A, 10) |  |
| desipramine |  |  |
| nortriptyline |  |  |
| imipramine |  |  |
| amitriptyline |  |  |
| butabarbitral |  |  |
| pentobarbital | 20 (4A) |  |
| secobarbital | 17 (10) |  |
| phenobarbitol |  |  |
| amobarbital |  |  |

D. Comparative Chromatographic Baselines

Extracts of blank urine samples run on the high purity SDVB column, using methods described in the Examples, in each case provided cleaner chromatographic baselines than blank extracts run on commercial PMMA columns, using extraction methods provided by the manufacturer. Possible interference with analysis, as well as instrument down time, is thus reduced by use of the present system. This is illustrated in FIGS. 2–11, which show GC-MS scans of drug-spiked samples and blank samples, for both the high purity SDVB column and the PMMA column, as summarized below:

| FIG. | Column | Analyte(s) | Sample or Blank |
|---|---|---|---|
| 2A | SDVB | THC—COOH | Sample (30 ng/ml) |
| 2B |  |  | Blank |
| 3A | PMMA | THC—COOH | Sample (30 ng/ml) |
| 3B |  |  | Blank |
| 4A | SDVB (hydrolyzed); | Codeine | Sample |
| 4B |  | Morphine | 300 ng/ml each |
| 4C |  | Codeine | Blank (hydrolyzed) |
| 4D |  | Morphine |  |
| 5A | PMMA (hydrolyzed); | Codeine | Sample |
| 5B |  | Morphine | 300 ng/ml each |
| 5C |  | Codeine | Blank (hydrolyzed) |
| 5D |  | Morphine |  |
| 6A | SDVB (unhydrolyzed); | Codeine | Sample |
| 6B |  | Standard | 300 ng/ml each |
| 6C |  | Morphine |  |

-continued

| FIG. | Column | Analyte(s) | Sample or Blank |
|---|---|---|---|
| 7A | | Codeine | Blank |
| (unhydrolyzed) | | | |
| 7B | | Standard | |
| 7C | | Morphine | |
| 8A | PMMA | Codeine | Sample |
| (unhydrolyzed); | | | |
| 8B | | Standard | 300 ng/ml each |
| 8C | | Morphine | |
| 9A | | Codeine | Blank |
| (unhydrolyzed) | | | |
| 9B | | Standard | |
| 9C | | Morphine | |
| 10A | SDVB | Amphetamine | Sample; |
| 10B | | Amph. standard | 300 ng/ml |
| each | | | |
| 10C | | Methamphetamine | |
| 10D | | Meth. standard | |
| 11A | | Amphetamine | Blank |
| 11B | | Amph. standard | |
| 11C | | Methamphetamine | |
| 11D | | Meth. standard | |

Extractions were carried out according to the manufacturer's procedures for the PMMA column, and according to procedures given in the following Examples for the SDVB column: THC-COOH, Example 1; opiates, Example 6E; and amphetamine/methamphetamine, Example 8.

When examining the figures, differences in vertical scale, as indicated in the upper left hand corner of each scan, must be taken into account. For example, in FIGS. 2A–2B, the size of the peaks in the lower figure is magnified approximately three times (1.79%/0.56%) with respect to the upper figure. Thus, the amount of potential interference with THC-COOH shown in the blank sample is probably negligible as compared to the sample peak, with the drug present at 30 ng/ml.

The corresponding pair of figures for the PMMA column, however (FIGS. 3A–3B, THC-COOH sample and blank), show a more significant potentially interfering signal in the blank sample (shown at less than twice the scale of the sample scan).

Figures 8A, 8B, 8C:
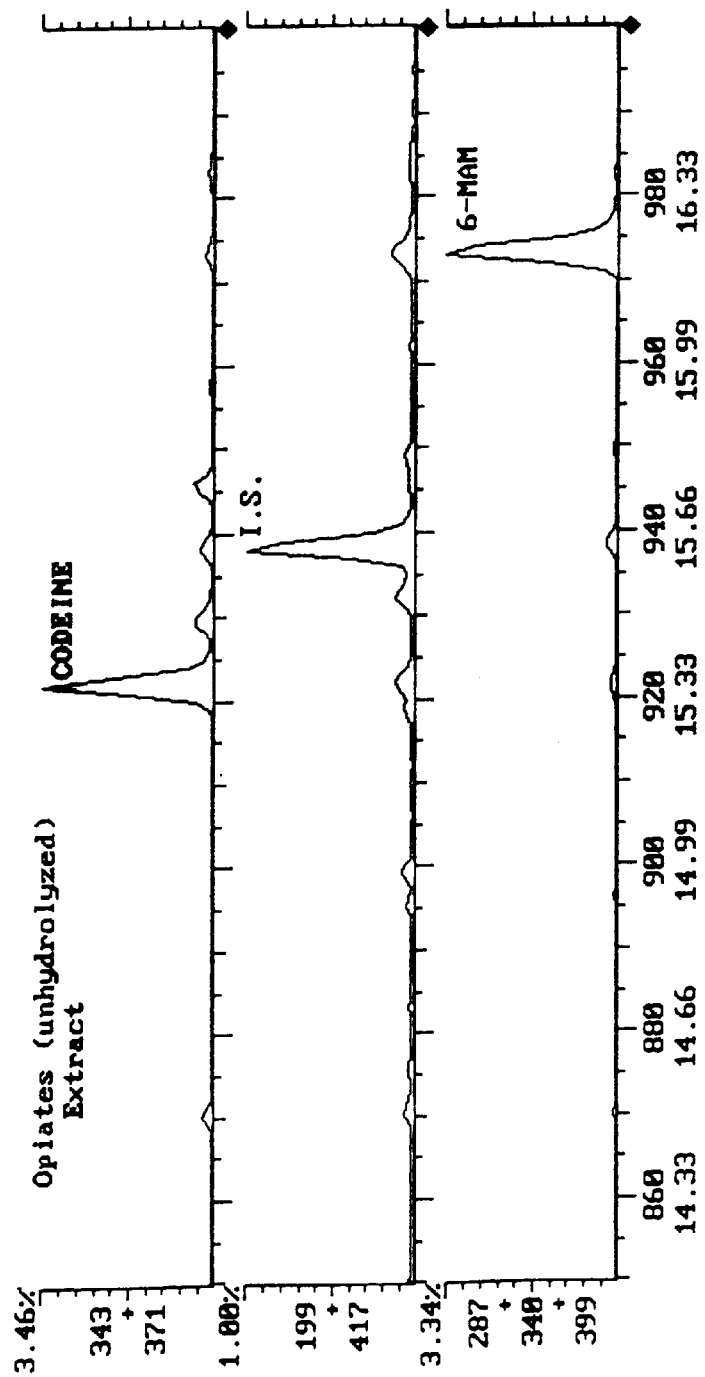
FIGS. 8A–8C show the corresponding regions of a GC-MS scan of a PMMA extract, prepared in accordance with the manufacturer's instructions, of an unhydrolyzed urine sample spiked with codeine and morphine as in FIGS. 6A–6C.
Figures 10A, 10B, 10C, 10D:
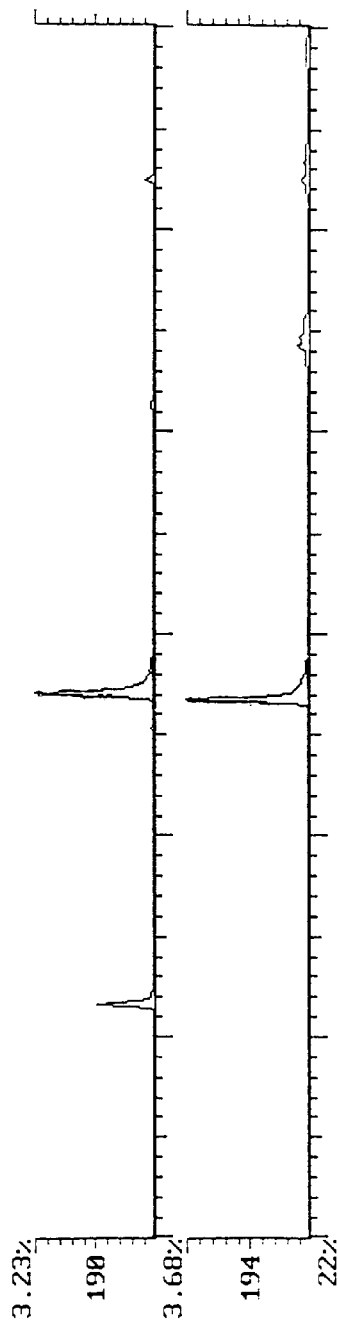
FIGS. 10A–10D show the amphetamine (B), methamphetamine (D) and internal standard (A,C) ion regions of a GC-MS scan of an SDVB extract of a urine sample spiked with each of these drugs at the NIDA detection cutoff level (300 ng/ml)

With respect to the remaining scans, blank extracts for the hydrolyzed opiate extractions show potential interference for both columns (FIGS. 4C–D and 5C–D), but the interfering peak for morphine from the PMMA column is much more significant than for the SDVB column (FIGS. 5D and 4D, respectively). Little or no interference was seen in the blank scans for the hydrolyzed extracts on SDVB (FIGS. 7A–7C), while an interfering peak is clearly seen with respect to morphine in the PMMA blank extract (FIG. 9A), at approximately four times the scale of the sample extract (FIG. 8A). Finally, although potential interference is seen with respect to methamphetamine, and its deuterated standard, in the SDVB blank extracts (FIGS. 11C–11D), it should be noted that the scale of these scans is on the order of hundreds of times greater than the corresponding sample scans (FIGS. 10C–D).

Figure 12A:
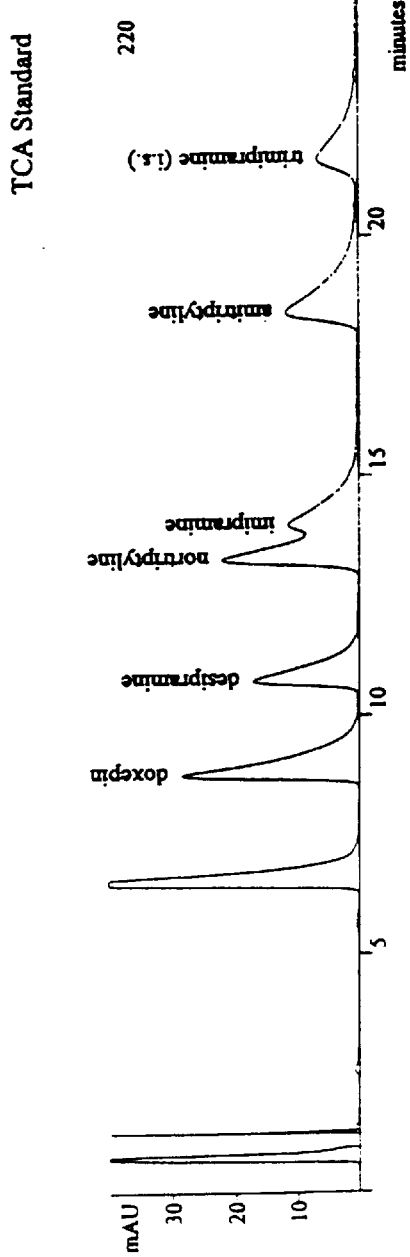
FIGS. 12A–12C show HPLC traces of (A) a standard TCA drug mixture, (B) an SDVB extract of a urine sample with each of these drugs added at 500 ng/ml, and (C) an SDVB extract of a blank urine sample, without added drugs.
Figure 12B:
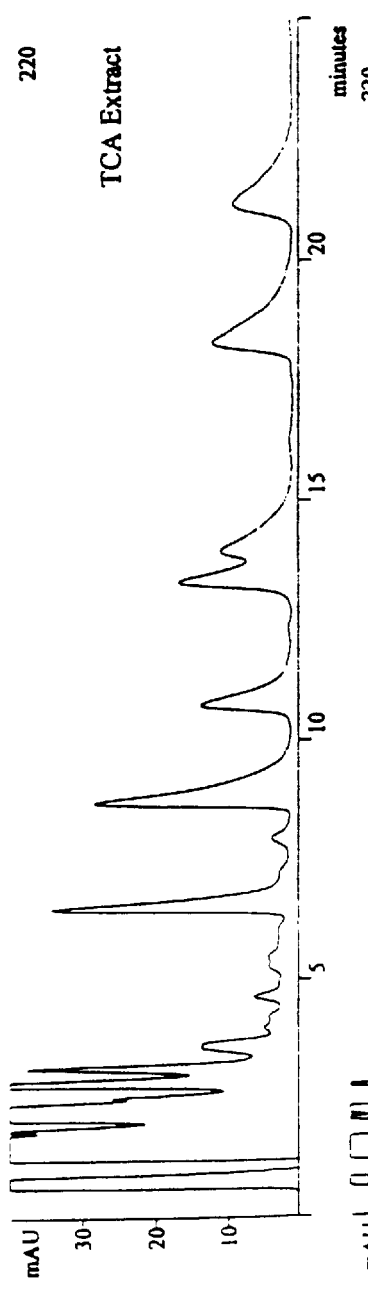
Figure 12C:
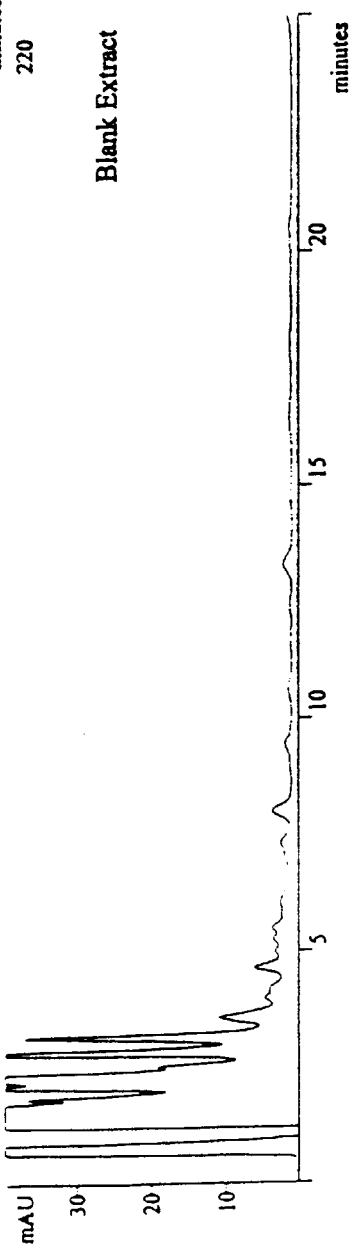

FIGS. 12A–12C show HPLC scans of (A) a TCA standard solution and SDVB extracts of (B) a urine sample spiked with the drugs (500 ng/ml each) and (C) a blank extract. Again, little or no interference was seen in the blank baseline scan.

EXAMPLES

The following examples illustrate but are not intended in any way to limit the invention.

Materials and Methods

A 9×1 cm column packed with 50 mg high purity underivatized SDVB resin (Varian Bond Elut™ ABS Elut resin), giving an adsorbent bed height of about 5 mm, was used for the extractions. The resin had an average particle size of about 125 μm and an average pore size of about 450Å.

In each example, the urine sample was optionally spiked with a known quantity of the substance(s) being analyzed. Recovery of sample in the eluate was quantitated by comparison with a known quantity of internal standard added to the eluate before analysis.

Unless otherwise indicated, the buffer used was 0.1M $KH_2PO_4$, pH 6. Ammonium hydroxide ($NH_4OH$) was a 30% aqueous stock solution.

Unless otherwise indicated, a DB5-ms column, 30 m×250 μm was used for GC-MS analysis, using the following temperature gradient: from 100° C. to 280° C. at 10° C./minute, then hold at 280° C. for 12 minutes.

Summary of Solvent Systems

1. Wash: 2 ml 5% aqueous acetonitrile containing it ammonium hydroxide
   Elution: 1 ml ethyl acetate:isopropanol (85:15)
2A. Wash: 3 ml 0.1M $KH_2PO_4$ (pH 6)
   Elution: 1 ml acetonitrile:n-butylchloride (3:7)
2B. Wash: 3 ml 0.1M $KH_2PO_4$ (pH 6)
   Elution: 2 ml acetone:$CHCl_3$ (1:1)
3. Wash: 2 ml of 5% aqueous methanol (95:5 MeOH:$H_2O$)
   Elution: 2 times with 0.75 ml methanol
4A. Wash: 1 ml 0.1M $KH_2PO_4$ (pH 6)
   Elution: 2 ml hexane:ethyl acetate (3:1)
4B. Wash: 1 ml 0.1M $KH_2PO_4$ (pH 6):acetonitrile (9:1)
   Elution: 2 ml acetone: $CHCl_3$ (1:1)
5A. Wash: 1 ml 0.1M $KH_2PO_4$ (pH 6):acetonitrile (9:1)
   Elution: 2 ml acetone:$CH_2Cl_2$ (1:1)
5B. Wash: 1 ml 0.1M $KH_2PO_4$ (pH 6):acetonitrile (9:1)
   Elution: 2 ml acetone:$CHCl_3$ (1:1)
6A. Wash: 3 ml 0.1M $KH_2PO_4$ (pH 6)
   Elution: 2 ml acetone:$CHCl_3$ (7:3)
6B. Wash: 3 ml 0.1M $KH_2PO_4$ (pH 6)
   Elution: 1.5 ml MeOH with 2% $NH_4OH$
6C. Wash: 3 ml 0.1M $KH_2PO_4$ (pH 6)
   Elution: 2 ml acetone:$CHCl_3$ (1:1)
6D. Wash: 3 ml 0.1M $KH_2PO_4$ (pH 6)
   Elution: 2 ml 2% $NH_4OH$ in acetone:$CHCl_3$ (7:3)
6E. pH of hydrolyzed urine adjusted to 6
   Wash: 2 ml 7% aqueous methanol (7:93 MeOH:$H_2O$)
   Elution: 1.5 ml n-BuCl:ethyl acetate (1:1) containing 1% $NH_4OH$
6F. pH of hydrolyzed urine adjusted to 8.4
   Wash/Elution: same as 6F
7. Wash: 1 ml 0.1M $KH_2PO_4$ (pH 6)
   Elution: 2 ml acetone:$CHCl_3$ (1:1)
8. Wash: 1 ml 0.1M $KH_2PO_4$ (pH 6):acetonitrile (9:1)
   Elution: 2 ml acetone:$CHCl_3$ (1:1)

9A. Wash: 3 ml 0.1 M $KH_2PO_4$
Elution: 2 ml $CH_2Cl_2$:isopropanol (80:20)

9B. Wash: 3 ml 5% aqueous methanol (95:5 $MeOH:H_2O$)
Elution: 2 ml $CH_2Cl_2$:isopropanol (80:20)

9C. Wash: 3 ml 0.1 M $KH_2PO_4$
Elution: 2 ml $CH_2Cl_2$:isopropanol:$NH_4OH$ (78:20:2)

9D. Wash: 3 ml 0.1 M $KH_2PO_4$
Elution: 2 ml methanol

10. Wash: 3 ml D.I water or 3 ml 5% aqueous methanol (95:5 $MeOH:H_2O$)
Elution: 2 ml ethyl acetate Extraction Procedures Example 1

Extraction Procedure for THC-COOH

To a 2 ml urine sample was added 400 μl of 10 M KOH. The solution was vortexed and heated in a 60° C. heater block for 20 minutes and then cooled to room temperature. A mixture of 0.2M acetate buffer, pH 4.0, containing 5% isopropanol (75%) and glacial acetic acid (25%) was added (2 ml), followed by thorough mixing.

The SDVB column was washed with 1 ml methanol, and the sample was added under gravity flow conditions. The column was then washed with 2 ml of a 5% aqueous acetonitrile solution containing 1% ammonium hydroxide, and dried by applying vacuum adjusted to at least 7" Hg for 5 minutes. The analyte was then eluted with 1 ml ethyl acetate:isopropanol (85:15).

An internal standard ($d_3$-THC-COOH) was added to the eluate, and the solvent was removed under nitrogen at room temperature. To the residue was added 50 μl of BSTFA (N,O-bis(trimethylsilyl)trifluoroacetamide) containing TMCS (trimethylchlorosilane), followed by vortexing. The mixture was incubated at 70° C. for 20 minutes and allowed to cool to room temperature. A sample was then injected onto the GC-MS column.

Example 2A

Extraction Procedure for Benzoylecgonine and Cocaine

In a large test tube, 2 ml urine was mixed with 2 ml buffer, and the pH was adjusted, if necessary, to between 5.0 and 7.0 by the addition of phosphoric acid.

The column was washed sequentially with 2 ml methanol and 2 ml buffer. The sample was poured into the column reservoir and drawn slowly through the column under a light vacuum. The column was then washed with 3 ml buffer and dried for 5 minutes at full vacuum. The analytes were eluted with 1 ml acetonitrile:n-butylchloride (3:7).

An internal standard (nalorphine) was added to the eluate, which was then evaporated to dryness under a slow stream of nitrogen. The analytes were derivatized by treating with 50 μl BSTFA containing 1% TMCS and heating at 70° C. for 20 minutes. A 1–2 μl aliquot was used for GC-MS analysis.

Example 2B

Alternate Extraction Procedure for Benzoylecgonine and Cocaine

The procedure in Example 2A was followed, except that 2 ml acetone:$CHCl_3$ (1:1) replaced acetonitrile:n-butylchloride as the eluting solvent.

Example 3

Amphetamine and Methamphetamine Extraction Procedure

A 2 ml urine sample was diluted with 1.5 ml buffer. The column was washed with 2 ml methanol, followed by 2 ml buffer. The sample was applied under gravity flow conditions, and the column was then washed with 2 ml of 5% aqueous methanol. The column was dried under vacuum of 5 inches Hg or higher, and the analytes were eluted with two 0.75 ml aliquots of methanol.

Internal standards ($d_5$-amphetamine and $d_5$-methamphetamine) were added to the eluate, followed by 30 μl of methanolic HCl (methanol:conc. HCl, 9:1). The eluate was evaporated to dryness under nitrogen, 50 μl pentafluoropropionic anhydride (PFPA) was added, and the solution was heated at 70° C. for 40 minutes. A 1 μl aliquot was used for GC-MS analysis, using the following temperature gradient: from 80° C. to 240° C. at 10° C./min, then hold at 240° C. for 4 min.

Example 4A

Extraction Procedure for Barbiturates

In a large test tube, a 2 ml urine sample was diluted with 2 ml buffer.

The column was washed with 1 ml MeOH, followed by 1 ml buffer, and the sample was applied under gravity flow conditions. The column was then washed with 1 ml buffer and dried by applying vacuum adjusted to at least 7" Hg for 5 minutes. The analyte was eluted with 2 ml of hexane:ethyl acetate (3:1).

The eluate was transferred into a Reacti-Vial and the solvent evaporated to dryness under nitrogen at room temperature. Internal standard solution ($d_5$-secobarbital) was added, followed by vortexing. A sample was then injected onto the GC-MS column.

Example 4B

Alternate Extraction Procedure for Barbiturates

The procedure described for Example 4A was followed, using 1 ml buffer/acetonitrile (9:1) as a wash and 2 ml acetone:$CHCl_3$ (1:1) for elution.

Example 5A

Extraction Procedure for PCP

In a large test tube, 2 ml urine was mixed with 2 ml buffer, and the pH was adjusted, if necessary, to between 5.0 and 7.0 by addition of phosphoric acid.

The column was washed sequentially with 2 ml methanol and 2 ml buffer. The sample was poured into the column reservoir and drawn slowly through the column under a light vacuum. The column was then washed with 1 ml of buffer:acetonitrile (9:1) and dried for 5 minutes at full vacuum. The analyte was eluted with 2 ml acetone:$CH_2Cl_2$ (1:1).

Internal standard (carbazole) was added to the eluate, which was then evaporated to dryness under a slow stream of nitrogen and reconstituted in 100 μl of ethyl acetate. A 1–2 μl aliquot of this solution was used for GC-MS.

Example 5B

Alternate Extraction Procedure for PCP

The procedure described in Example 5B was followed, except that 2 ml acetone:$CHCl_3$ (1:1) replaced acetone:$CH_2Cl_2$ as the eluting solvent.

Example 6A

Extraction Procedure for Opiates (unhydrolyzed)

To a 2 ml urine sample was added 1.5 ml buffer. The column was washed with 2 ml methanol, followed by 1.5 ml buffer. The sample was applied under gravity flow conditions, and the column was then washed with 3 ml buffer. The column was dried under vacuum for 5 minutes at 7 inches of Hg or higher, and the drug was then eluted with 2 ml of acetone:$CHCl_3$ (7:3).

The eluate was collected in, or transferred to, a Reacti-Vial™, and a deuterated internal standard, such as codeine-$d_3$, was added to the vial. The contents were evaporated to dryness under nitrogen, 50 μl of acetonitrile and 50 μl of BSTFA or MSTFA (N-methyl-N-trimethylsilyl trifluoroacetamide) containing 1% TMCS were added, and the contents were heated at 70° C. for 30 minutes. A 1 μl aliquot was injected into the GC column, using the following temperature gradient: 80° C. for 3.1 min, increase to 285° C. at 20° C./min, then hold at 285° C. for 5.85 min.

Examples 6B–D

Alternate Extraction Procedures for Opiates (unhydrolyzed)

The procedure described in Example 2A was followed, using the following solvents for elution in place of acetonitrile:n-butylchloride:

6B: 1.5 ml MeOH with 2% $NH_4OH$

6C: 2 ml acetone:$CHCl_3$ (1:1)

6D: 2 ml 2% $NH_4OH$ in acetone:$CHCl_3$ (7:3)

Example 6E

Extraction Procedure for Opiates (hydrolyzed)

To a 1 ml urine sample was added 0.25 ml of concentrated HCl. The sample was heated at 120° C. for 30 minutes and cooled to room temperature. To this solution was added 0.35 ml 10M KOH, followed by 1.5 ml of buffer.

The column was washed with 1 ml methanol, followed by 0.5 ml buffer. The sample was applied under gravity flow conditions, and the column was then washed with 2 ml of 7% methanol in water. The column was dried under vacuum for 5 minutes at 7 inches of Hg or higher, and the drug was then eluted with 1.5 ml ethyl acetate:n-butylchloride (1:1) containing 1% ammonium hydroxide.

The eluate was collected, treated and analyzed as described for Example 6A above.

This method was also found effective, omitting the hydrolysis step, for the free opiates codeine (recovery 90%) and 6-MAM (recovery 89%).

Example 6F

Alternate Extraction Procedure for Opiates (hydrolyzed)

The procedure described for Example 6E was followed, except that the pH of hydrolyzed urine was adjusted to 8.4 before applying it to the column.

Example 7

Extraction Procedure for Benzodiazepines

The urine sample was prepared, the column conditioned, and the sample applied to the column as described for Example 2A. The column was then washed with 2 ml buffer and dried for 5 minutes at full vacuum. The analyte was eluted with 2 ml acetone:$CHCl_3$ (1:1).

Internal standard (nalorphine) was added to the eluate, which was then evaporated to dryness under a slow stream of nitrogen. The analytes were derivatized by treating with 50 μl BSTFA+1% TMCS and heating at 70° C. for 20 minutes. A 1–2 μl aliquot was used for GC-MS analysis.

Example 8

Extraction Procedure for LSD

The urine sample was prepared, the column conditioned, and the sample applied to the column as described for Example 2A. The column was then washed with 1 ml of buffer:acetonitrile (9:1) and dried for 5 minutes at full vacuum. The analyte was eluted with 2 ml acetone:$CHCl_3$ (1:1). An internal standard ($d_3$-LSD) was added, the eluate was evaporated to dryness under a slow stream of nitrogen, and the analytes were derivatized as described in Example 7 above.

This procedure also gave good recoveries for THC-COOH (91%), cocaine/benzoylecgonine (100%), barbiturates (87–100%), PCP (100%), and opiates (75–85%).

Example 9A

Extraction Procedure for Tricyclic Antidepressants

The urine sample was prepared, the column conditioned, and the sample applied to the column as described for Example 2A. The column was then washed with 2 ml of buffer and dried for 5 minutes at a vacuum of 5 inches Hg or greater. The analyte was eluted with 2 ml $CH_2Cl_2$:isopropanol (80:20).

Internal standard (trimipramine) was added to the eluate, and the solution was evaporated to dryness under nitrogen. The dried eluate was redissolved in 70 μl of methanol and 130 μl of mobile phase B, below (0.01M $KH_2PO_4$). A 90 μl sample was analyzed by HPLC using diode array detection (DAD), as follows:

Column: Varian TCA, 4.6 mm×15 cm

Mobile phase: A: 80:20 acetonitrile:0.01M $KH_2PO_4$ (pH 6) B: 0.01M $KH_2PO_4$ (pH 6)

Gradient: isocratic—38% A:62% B

Flow rate: 1.3 ml/min

Detection: UV at 220 nm

Example 9B–D

Alternate Extraction Procedures for Tricyclic Antidepressants

The procedure described in Example 9A was used, with the following substitutions:

9B. Wash: 3 ml of 5% aqueous methanol

9C. Elution: 2 ml $CH_2Cl_2$:isopropanol:$NH_4OH$ (78:20:2)

9D. Elution: 2 ml methanol

Example 10

General Extraction/Screening Procedure for Drugs of Abuse

This procedure provides good recoveries for a large spectrum of drugs and/or metabolites, including THC-COOH, opiates, amphetamines, barbiturates, PCP, LSD, cocaine, and benzodiazepines, as shown above in Table II.

In a large test tube, 2 ml urine was mixed with 2 ml buffer, and the pH was adjusted, if necessary, to between 5.0 and 7.0 by the addition of phosphoric acid.

The column was washed sequentially with 2 ml methanol and 2 ml buffer. The sample was poured into the column reservoir and drawn slowly through the column under a light vacuum.

The column was washed with 3 ml of D.I. water or, alternatively, 3 ml of 5% aqueous methanol (5:95 MeOH:$H_2O$), and dried for 5 minutes at full vacuum. The analytes were then eluted with 2 ml of ethyl acetate. Internal standards and/or derivatizing reagents were added to the eluate, and the analytes determined by methods described in Examples 1–9 above.

While the invention has been described with reference to specific methods and embodiments, it will be appreciated that various modifications, particularly in regard to modifications in the volumes of dilution, conditioning, wash, and elution solvents, may be made without departing from the invention.

It is claimed:

1. A diagnostic method comprising:

contacting an aqueous body fluid sample suspected of containing an analyte selected from cocaine or benzoylecgonine with a substantially underivatized styrene-divinyl benzene resin adsorbent, thereby adsorbing said analyte to the adsorbent, washing the adsorbent with a first solvent system consisting of an aqueous buffer having a pH in the range of about 4.5 to about 6.5, applying a second solvent system, consisting of acetone/chloroform in a ratio of about 1:1 by volume or acetonitrile/n-butylchloride in a ratio of about 3:7 by volume, to the adsorbent, effective to selectively elute the analyte from the adsorbent, thereby producing an eluate containing about 80% or more of the analyte present in said sample, said eluate being suitable, without further purification, for gas chromatographic analysis of said analyte, and detecting or quantitating the analyte contained in the eluate.

* * * * *